(12) United States Patent
Carlson

(10) Patent No.: US 9,983,121 B2
(45) Date of Patent: May 29, 2018

(54) PHOTONIC SENSOR TRACKING

(71) Applicant: FAZ TECHNOLOGY LIMITED, Dublin (IE)

(72) Inventor: Douglas O. Carlson, Winter Garden, FL (US)

(73) Assignee: FAZ TECHNOLOGY LIMITED (IE)

( * ) Notice: Subject to any disclaimer, the term of this patent is extended or adjusted under 35 U.S.C. 154(b) by 109 days.

(21) Appl. No.: 14/693,947

(22) Filed: Apr. 23, 2015

(65) Prior Publication Data

US 2016/0313235 A1   Oct. 27, 2016

(51) Int. Cl.
| | |
|---|---|
| G01N 21/00 | (2006.01) |
| G01N 21/25 | (2006.01) |
| G01D 5/353 | (2006.01) |
| G01M 11/00 | (2006.01) |

(52) U.S. Cl.
CPC ....... *G01N 21/255* (2013.01); *G01D 5/35316* (2013.01); *G01D 5/35396* (2013.01); *G01M 11/31* (2013.01); *G01N 2201/0612* (2013.01); *G01N 2201/088* (2013.01)

(58) Field of Classification Search
CPC .......... G01D 5/35316; G01D 5/35396; G01N 21/255; G01N 2201/0612; G01M 11/31
USPC ...................................... 356/73.1
See application file for complete search history.

(56) References Cited

U.S. PATENT DOCUMENTS

| | | | |
|---|---|---|---|
| 2008/0177482 A1* | 7/2008 | Kishida ................. | G01B 11/16 702/35 |
| 2009/0122319 A1* | 5/2009 | Ronnekleiv ............ | G01H 9/004 356/477 |
| 2012/0083705 A1* | 4/2012 | Yuen .................... | A61B 5/0002 600/508 |
| 2014/0125363 A1* | 5/2014 | Bock .................... | G01R 31/28 324/750.02 |

OTHER PUBLICATIONS

Misas, C. J., J. M. Lopez-Higuera, and M. Lopez-Amo. "Adaptive filters applied to the interrogation of photonic sensors." IEEE Sensors Journal 6.3 (2006): 748.*
Jauregui, Cesar, et al. "Digital adaptative filters for interrogating fiber optic sensors." Bruges, Belgium-Deadline Past. International Society for Optics and Photonics, 2005.*

(Continued)

*Primary Examiner* — Hina F Ayub
(74) *Attorney, Agent, or Firm* — Polsinelli PC

(57) ABSTRACT

A device and method for tracking a spectral response. The device and method including inputting light to a waveguide medium having a plurality of perturbation sensors disposed in a spaced relationship in the waveguide medium; receiving a plurality of signals reflected from the plurality of perturbation sensors; retrieving from the received signals, data representing a plurality of signal values, each signal value comprising at least a magnitude value and a wavelength value; identifying within the plurality of signal values, at least a first signal value and a second signal value, being in an overlap state; estimating, for at least some of the plurality of perturbation sensors, an expected signal value; associating each expected signal value with a respective signal value from the plurality of signal values; updating each expected signal value with the associated signal value.

27 Claims, 3 Drawing Sheets

(56) References Cited

OTHER PUBLICATIONS

Bolzon, G., R. Fedele, and G. Maier. "Parameter identification of a cohesive crack model by Kalman filter." Computer Methods in Applied Mechanics and Engineering 191.25 (2002): 2847-2871.*
Treiber, Johannes, et al. "Filtering techniques in the dynamic deformation estimation using multiple strains measured by FBGs." The 15th International Symposium on: Smart Structures and Materials & Nondestructive Evaluation and Health Monitoring. International Society for Optics and Photonics, 2008.*

* cited by examiner

PHOTONIC SENSOR TRACKING

BACKGROUND

Field of Invention

The present disclosure generally relates to a method and device for tracking the reflected or transmitted spectral response of a perturbation sensor and more particularly to a method and device for tracking the spectral response of a perturbation sensor in an overlap condition.

Description of Related Art

Fiber Bragg grating sensors offer broad improvements to current systems for monitoring temperature and stress. For example, the oil and gas industry often requires the monitoring of the downhole environment of drilling sites. While the oil and gas industry often employs distributed temperature sensors and distributed acoustic sensors to measure temperature and stress, these sensors have undesirable long integration times (e.g., greater than five minutes). Fiber Bragg grating sensors, by contrast, are only limited to the time it takes signals to reflect from the sensors and return to the transceiver system, which is less than 10 microseconds per kilometer. Furthermore, fiber Bragg grating sensors offer the advantage of a much higher signal-to-noise ratio over other known solutions.

However, as temperature, strain, vibration, pressure, and acoustic signals vary around a fiber Bragg grating sensor, the reflected signal will vary in at least wavelength and magnitude. As shown in FIG. 1, subjected to enough temperature or stress, the wavelength of a reflected signal may vary to the point where it is overlapping the reflected signal of a separate fiber Bragg grating sensor. This overlap condition may introduce ambiguity into the measurement of the spectral response of a plurality of fiber Bragg grating sensors. More specifically, this may limit the number of sensors per fiber because the sensors need to be spaced such that the signal from one sensor will not overlap another. This ambiguity and resulting required spacing may limit the spatial resolution and the effectiveness of the fiber Bragg grating sensors.

Accordingly, there is a need in the art for a method and/or device that will accurately track the signals of a perturbation sensor in an overlap condition to reduce or eliminate ambiguity.

SUMMARY OF THE INVENTION

The present disclosure is directed to inventive methods and apparatus for tracking the responses of perturbation sensors in overlap conditions. Various embodiments and implementations herein are directed to a method and device in which a signal detector, a tracking filter, and an overlap detector are in communication with fiber optic cable, having a plurality of perturbation sensors. Using the various embodiments and implementations herein, the signal responses of perturbation sensors in an overlap condition may be tracked. In an exemplary aspect, a method for tracking a spectral response comprises inputting light to a waveguide medium having a plurality of perturbation sensors disposed in a spaced relationship in the waveguide medium; receiving a plurality of signals from the plurality of perturbation sensors; retrieving from the received signals data representing a plurality of signal values, each signal value comprising at least a magnitude value and a wavelength value; identifying within the plurality of signal values at least a first signal value and a second signal value being in an overlap state; estimating, for at least some of the plurality of perturbation sensors, an expected signal value; associating each expected signal value with a respective signal value from the plurality of signal values; and updating each expected signal value with the associated signal value.

According to an embodiment, the waveguide medium is an optical fiber.

According to an embodiment, the receive signals each comprises at least a portion of a full signal waveform.

According to an embodiment, the method further includes, before the step of associating, the steps of: substituting the magnitude value of the first signal value with a previously received magnitude of the first reflected signal; and substituting the magnitude value of the second reflected signal with a previously received magnitude of the second reflected signal.

According to an embodiment, the method further comprises the steps of: adding to the plurality of signal values a first extended signal value having a wavelength value equal to the wavelength of the first signal value and a magnitude value equal to the previously received magnitude of the second signal value; and adding to the plurality of signal values a second extended signal value having a wavelength value equal to the wavelength of the second signal value and a magnitude value equal to the previously received magnitude of the first signal value.

According to an embodiment, the step of associating comprises the steps of calculating an error value between each expected signal value and each signal value in the plurality of signal values; and assigning each expected signal value to the signal value with a smallest error value.

According to an embodiment, the step of calculating an error comprises determining an innovation for each expected signal value and each signal value from the plurality of signal values.

According to an embodiment, the step of associating comprises the step of: calculating an error between an expected signal value and any signal value, from the plurality of signal values, within a predetermined interval of the estimated signal; and assigning the expected signal value to the signal value within the interval with a smallest error.

According to an embodiment, the step of identifying the overlapped signals comprises: determining whether the difference between the wavelength of any signal value from the plurality of signal values and any other signal value from the plurality of values is less than a predetermined value.

According to an embodiment, the steps of estimating and updating are each performed by a Kalman filter.

According to an embodiment, the steps of estimating and updating are each performed by an alpha beta filter.

According to an embodiment, the steps of estimating and updating are each performed by a particle filter.

In another aspect, a device for tracking a spectral response includes a non-transitory storage medium configured to receive data representing a plurality of signal values, each signal value having a magnitude value and a wavelength value; identify within the plurality of signal values at least a first signal value and a second signal value being in an overlap state; estimate, for at least some of the plurality of perturbation sensors, an expected signal value; associate each expected signal value with a respective signal value from the plurality of signal values; and update each expected signal value with the associated signal value.

According to an embodiment, the data is received from signals reflected by the plurality of perturbation sensors and propagated in a waveguide medium.

According to an embodiment, the received signals each comprise at least a portion of a full signal.

According to an embodiment, the device is, before associating, further configured to: substitute the magnitude value of the first signal value with a previously received magnitude of the first reflected signal; and substitute the magnitude value of the second reflected signal with a previously received magnitude of the second reflected signal.

According to an embodiment, the device is further configured to add to the plurality of signal values a first extended signal value having a wavelength value equal to the wavelength of the first signal value and a magnitude value equal to the previously received magnitude of the second signal value; and add to the plurality of signal values a second extended signal value having a wavelength value equal to the wavelength of the second signal value and a magnitude value equal to the previously received magnitude of the first signal value.

According to an embodiment, associating comprises: calculating an error value between each expected signal value and each signal value in the plurality of signal values; and assigning each expected signal value to the signal value with a smallest error value.

According to an embodiment, calculating an error comprises determining an innovation for each expected signal value and at least one signal value from the plurality of signal values.

According to an embodiment, associating comprises: calculating an error between an expected signal value and any signal value, from the plurality of signal values, within a predetermined interval of the estimated signal; and assigning the expected signal value to the signal value within the interval with a smallest error.

According to an embodiment, identifying the overlapped signals comprises: determining whether the difference between the wavelength of any signal value from the plurality of signal values and any other signal value from the plurality of values is less than a predetermined value.

According to an embodiment, the steps of estimating and updating are each performed by a Kalman filter.

According to an embodiment, the steps of estimating and updating are each performed by an alpha beta filter.

According to an embodiment, the steps of estimating and updating are each performed by a particle filter.

These and other aspects of the invention will be obvious from the figures and detailed description below.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE VARIOUS EMBODIMENTS

The present disclosure is directed to inventive methods and apparatus for tracking the responses of perturbation sensors in overlap conditions. Various embodiments and implementations herein are directed to a method and device in which a signal detector, a tracking filter, and an overlap detector are in communication with fiber optic cable having a plurality of perturbation sensors. Using the various embodiments and implementations herein, the signal responses of perturbation sensors in an overlap condition may be tracked.

Figure 1:
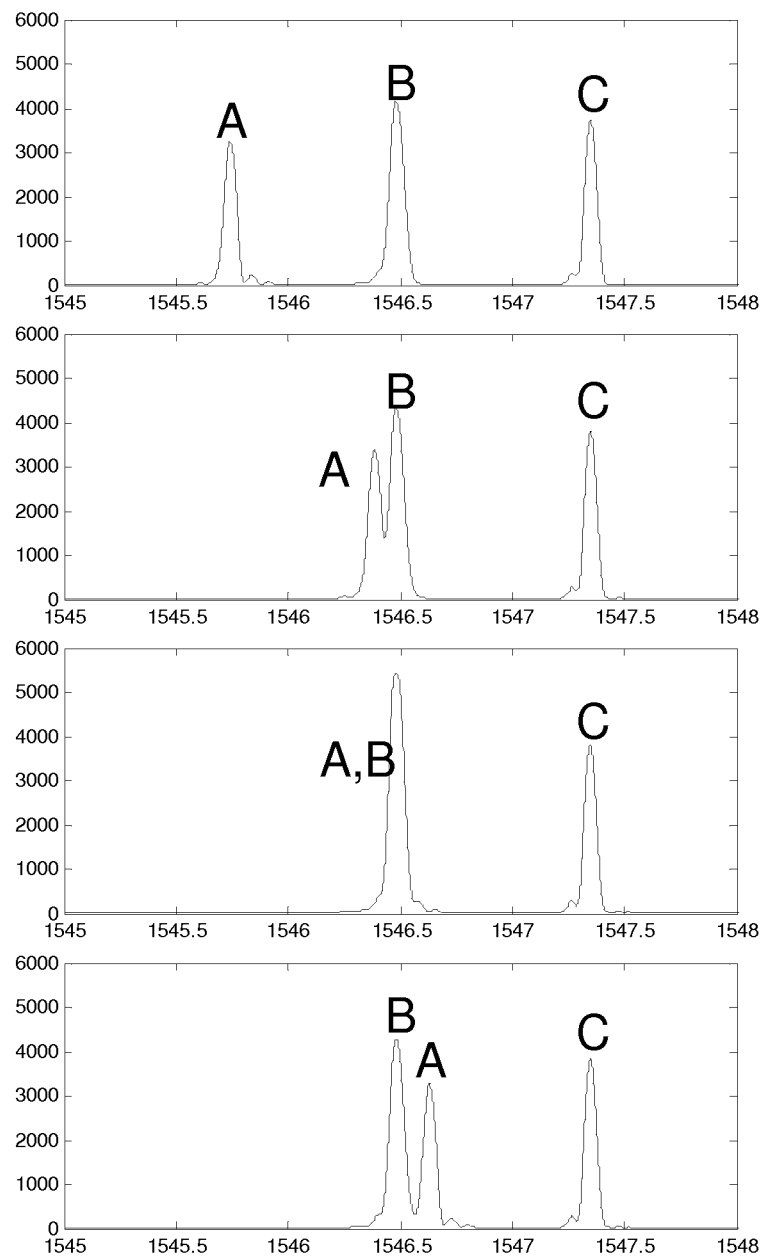
FIG. 1 shows a series of plots depicting an overlap condition of reflected signals from a perturbation sensor.
Figure 2:
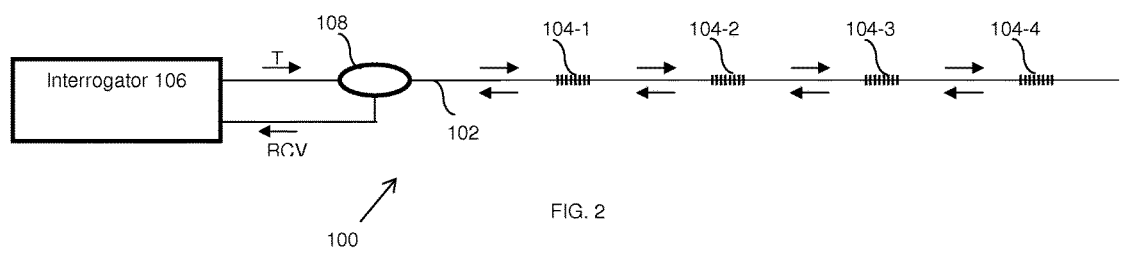
FIG. 2 shows a system for sending and receiving signals from a perturbation sensor, according to an embodiment.
Figure 3:
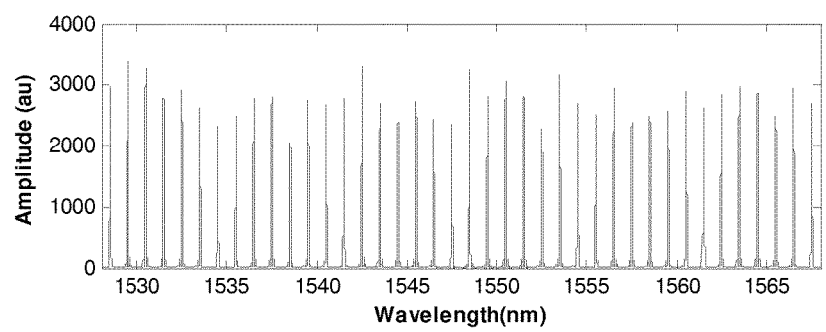
FIG. 3 shows a plot depicting a series of received signals according to an embodiment.
Figure 4:
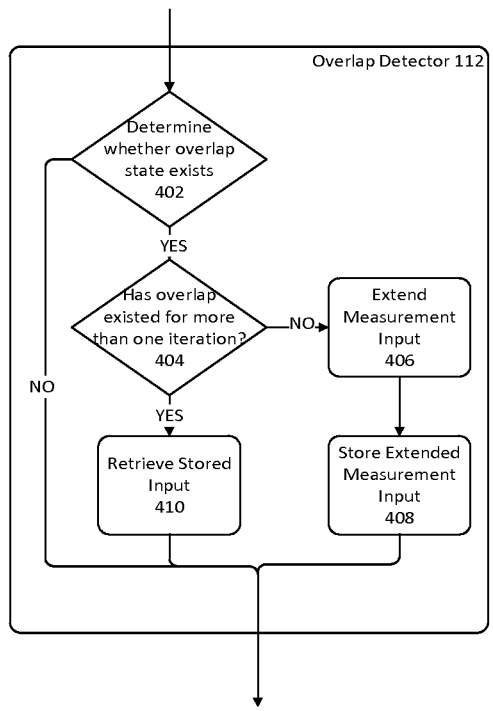
FIG. 4 shows a flowchart of a process implemented by an overlap detector according to an embodiment.

Referring to the drawings wherein like reference numerals refer to like parts throughout, FIG. 2 shows, according to a non-limiting embodiment, a system 100 for tracking perturbation sensors in an overlap condition. System 100 comprises a fiber optic cable 102 having a plurality of perturbation sensors 104-1, 104-2, 104-3, and 104-4 disposed in a spaced relationship, an interrogator 106, and a coupler 108. For the purposes of this disclosure, a perturbation sensor is any device or modification to a waveguide medium (the waveguide medium, in an exemplary embodiment, may be a fiber optic cable) configured to reflect or transmit a signal having properties that may vary in response to perturbations in or around the waveguide medium. Examples of perturbations sensors may include fiber Bragg gratings, Fabry-Perot interferometers, fibers lasers, MCF, and other sensors as will be appreciated by a person of ordinary skill in the art in conjunction with a review of this disclosure. While some perturbation sensors may reflect spectral content radiated through the waveguide medium, others may transmit or otherwise generate spectral content. It should be further appreciated that although the figures depict fiber Bragg gratings, these may be replaced with other forms of perturbation sensors as defined in this disclosure. Although a fiber optic cable is shown, it should be understood that any waveguide medium capable of transmitting an optic signal, and housing or effecting a perturbation sensor, may be used. Furthermore, although the waveguide medium is depicted as straight, it may be curved, arced, or looped, as will be appreciated by a person of ordinary skill in the art. For example, the waveguide medium may be looped back, and any signal transmitted by a perturbation sensor may be received at the end of the looped-back portion of the waveguide medium. Furthermore, although four sensors 104-1, 104-2, 104-3, and 104-4 are shown, it should be understood that any number of sensors may be used, and the number of sensors may vary according to the various needs of the system, including, but not limited to, required spatial resolution, fiber optic length, and system transmitting and receiving power. For example, in an exemplary embodiment as shown in FIG. 3, 40 response signals are shown from 40 perturbation sensors.

In an exemplary embodiment, each perturbation sensor 104 may have a unique reflection or transmission wavelength, and be spaced equidistant from each adjacent sensor's reflection or transmission wavelength, under constant temperature and stress. For example, for a constant temperature, and even stress throughout the line, the reflected or transmitted wavelength difference between adjacent perturbation sensors may be one nanometer (1 nm). Thus as shown in FIG. 3, if a laser having a varying frequency were inputted to the fiber optic cable, the line may reflect light at wavelengths: 1530.5, 1531.5, 1532.5, etc. In an alternative embodiment, the reflected or transmitted signals may be spaced every 2 nm, or any other amount as required by the needs of the particular application. Furthermore, one of ordinary skill in the art will recognize that the periodicity of the sensors may not be constant; they may be grouped in clusters or patterns as required by the system's application. In an exemplary embodiment, each received signal will be at least a portion of a full signal waveform, such as the peak or a peak portion of the signal.

System 100 may also comprise an interrogator 106 including an optical transmitter and receiver. The optical transmitter may include a laser diode optically connected to transmit a laser through fiber optic cable 102. The optical transmitter may be configured to vary the frequency of the laser diode over a predetermined range of wavelengths. According to an exemplary embodiment, optical transmitter of interrogator 106 would be capable of sweeping an optical signal over a range of 40 nm. An exemplary interrogator is a FAZ Vx Interrogator (FAZ Technology Research, Inc). However, one of ordinary skill in the art will recognize that other now known or later created interrogators having suitable performance characteristics may be used, which can transmit an optical signal through a fiber optic cable. Furthermore, the interrogator 106 may comprise a receiver capable of collecting reflected or transmitted light from a perturbation sensor. For example, in an embodiment, interrogator 106 may be capable of collecting 40000 samples over 40 nm in 1 ms via an A/D converter with resolution less than or equal to 1 picosecond. One of ordinary skill in the art will recognize that the requirements of the receiver may vary according to the requirements of the system's application.

Finally, interrogator 106 may comprise a signal detector for recognizing and collecting signals reflected or transmitted from perturbation sensors 104. In one embodiment, the signal detector may comprise an A/D converter with a threshold detector for sampling the received signals and detecting any signals above the predetermined threshold. One of ordinary skill will recognize that any signal detector sufficient for sampling and detecting received signals from the perturbation sensors 104 may be used. In an exemplary embodiment, the signal detector may output a measurement vector describing at least the wavelength and magnitude of each signal received from perturbation sensors 104, described in equation form as:

$$Z_k = \begin{pmatrix} \cdots & \lambda_i & \cdots \\ \cdots & r_i & \cdots \end{pmatrix}.$$

where i denotes a unique signal received from the perturbation sensors 104, λ represents signal wavelength, and r represents the magnitude (reflectivity) of the signal. In an exemplary embodiment, a quadratic fit may be used to estimate the peak of the signal wavelength $\lambda_i$ because the detected wavelength may not correspond to the actual wavelength due to sampling. Interrogator 106 may also be configured to transmit an optical signal and receive reflected or transmitted signals, outputting a measurement vector $Z_k$ at a predetermined interval. For example, interrogator 106 may be configured to output a measurement vector $Z_k$ once every 0.1 second. Each sweep and periodic output of a measurement vector $Z_k$, and all processes that follow each output of a $Z_k$ measurement vector may be referred to as an iteration.

Although the transmitter, receiver, and signal detector have been presented as part of interrogator 106, one of ordinary skill will readily recognize that the transmitter, receiver, and signal detector may be implemented as separate components.

The output from the signal detector, $Z_k$, in an exemplary embodiment, is input to a computing device containing a non-transitory storage medium suitable for implementing a tracking filter 110 and an overlap detector 112. Although FIG. 2 shows the signal detector and tracking filter implemented separate from interrogator 106, one of the ordinary skill will recognize that these components may be implemented on the same or separate computing devices.

According to an embodiment, the tracking filter is configured to receive and track each signal reflected or transmitted from a sensor 104 from iteration to iteration. For example, as fiber optic cable 102 is subjected to varying temperatures and stresses, the wavelength and magnitude of the reflected or transmitted signals may vary. Thus the values within measurement vector $Z_k$ will vary from iteration to iteration. Accordingly, tracking filter 110 is configured on each iteration to receive measurements $Z_k$, estimate the values of $Z_k$, associate the measurements with the estimates, and update the estimates with the associated $Z_k$ measurements. These updates are then used in the next iteration as the input to the estimation. In exemplary embodiments, tracking filter 110 may be implemented as a Kalman filter, an Alpha Beta filter, a Particle filter, or any other filter now known or later invented, capable of estimating the current state of a plurality of signals reflected or transmitted from a plurality of perturbation sensors, receiving a plurality of measurements representing the current state of the perturbation sensor signals, and updating the estimated signals with the measured signals. Furthermore, the tracking filter 110 may be implemented in other embodiments extending beyond a standard tracking filter such, but not limited to, a neural network or a max entropy scheme.

According to an embodiment, overlap detector 112 is positioned to receive $Z_k$ and detect any overlap states of measured signals within $Z_k$. Broadly, overlap detector 112 is configured to receive any measurement vector $Z_k$, to detect any overlap states of any two vectors within $Z_k$, to replace the magnitude of any signals in an overlap state with a previously received magnitude, and to extend the measurement vector, $Z_k$.

FIG. 3, shows a flowchart representing the process of overlap detector 112, according to an embodiment. In step 402, detector 112 determines whether an overlap state has occurred between two or more signals reflected or transmitted from perturbation sensor. In one embodiment, an overlap condition may occur when the difference in wavelength between two or more reflected or transmitted signals falls below a predetermined threshold. This may be expressed as $$d(\lambda_i, \lambda_j) < \epsilon, i \neq j$$

In an alternative embodiment, an overlap condition may occur where the number of measured states, i, is fewer than the number of estimated states. If an overlap condition has not occurred, the measurement vector $Z_k$ will be passed directly to the output of signal detector 112. If an overlap condition has occurred, the magnitude of $Z_k$ ceases to update until the overlap state ceases to occur. Thus if an overlap condition has not existed for more than one consecutive iteration, the magnitude of the signals in an overlap state, from measurement vector $Z_k$, may be stored (as shown in step 408). If an overlap condition has existed for more than one iteration, the stored magnitudes are retrieved, as shown in step 410, and the current measured magnitudes in $Z_k$ are replaced with the previously stored magnitudes. In this way, the originally stored magnitudes are passed to the output so long as the signals are in an overlap condition.

In an alternative embodiment, overlap detector 112, instead of determining whether the overlap condition has existed for more than one iteration, simply replaces the magnitudes of the signals in an overlap state with a predetermined magnitude. In one embodiment, the predetermined magnitude may be an average magnitude value for a set number of prior iterations of the signal in the overlap state. For example, the overlap detector could store each received magnitude for each signal, averaging each iteration with the previous iteration, to arrive at a mean magnitude for each signal. This mean magnitude of each signal could be used to replace the current measured magnitude for each overlapped signal. Alternatively, an arbitrary or set magnitude could be used as the predetermined magnitude.

According to an embodiment, in step 408, in an overlap state, the measurement vector is extended to include the case where the wavelength and reflectivity of signals in an overlap state have swapped, such that:

$$Z_k = \begin{pmatrix} Z_k \dfrac{\lambda_i}{r_j} \dfrac{\lambda_j}{r_i} \end{pmatrix}$$

This is to account for the condition that one of the overlapped signals has not passed through the other signal it is overlapped with, but has instead doubled back from the direction from which it came. For this condition, extending the measurement vector creates more measurement states for the association step, described in detail below.

Figure 5:
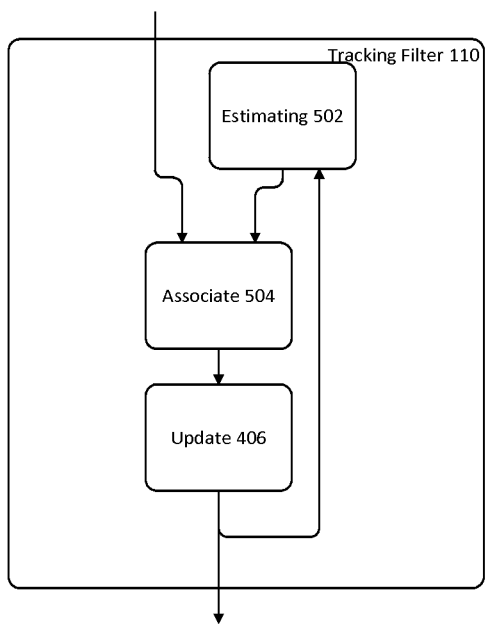
FIG. 5 shows flowchart of a process implemented by a tracking filter according to an embodiment.

In an exemplary embodiment, the output of overlap detector 112 is inputted to tracking filter 110. The process of tracking filter 110, according to one embodiment, is shown in FIG. 5 and broadly comprises the steps of estimating 502, associating 504, and updating 506. Tracking filters are generally well known in the art, and one of ordinary skill will recognize that any tracking filter may be selected suitable for tracking the reflections or transmissions of a plurality of perturbation sensors.

In step 502, tracking filter 110 estimates the current state of each fiber perturbation sensor 104. The process of this step will vary depending on the kind of tracking filter selected. Broadly, these tracking filters operate under an assumption of multiple linear kinematic models and a collection of multiple linear or nonlinear measurements models. For example, a Kalman filter may calculate an estimate according to a dynamic model called a plant model, and the most the recent updated value. In an exemplary embodiment, the output of step 502 is an estimate vector of wavelength and magnitude for each signal reflected or transmitted by the perturbation sensors 104.

In step 504, the estimation vector, output by step 502, and the measurement vector $Z_k$ output by overlap detector 112, are both input to step 504 to be associated. In this step, each estimated signal is associated with (assigned to) the actual measured value that was being estimated. According to one embodiment, an error measurement is found between each estimated value and each measured value, and the estimated value is assigned to the measured value with the smallest error value. In an exemplary embodiment, this error value is an innovation, defined by $\vec{v}_k \equiv \vec{z}_k - \hat{z}_{k|k-1}$, where $\vec{v}_k$ is the innovation value, $\vec{z}_k$ is the measurement vector, and $\hat{z}_{k|k-1}$ is the estimation vector. Thus the innovation represents the difference between the measurement vector and the estimation vector. In an alternative embodiment, only the difference between the measured magnitude and the estimated magnitude may be used. In yet another embodiment, only the difference between the measured wavelength and the estimated wavelength may be used to calculate the error. Furthermore, in one embodiment, an acceptance gate, as is known in the art, may be used to select which measurements are candidates for association. For example, an ellipsoid gate may be centered around the estimated target such that only measurements within a certain range of the wavelength and magnitude of the gate will be considered. One of ordinary skill in the art will recognize that any number of methods of association known in the art may be used, including, e.g., non-Bayesian nearest neighbor, global nearest neighbor, or Bayesian methods such as joint probabilistic data association or multiple hypothesis tracking.

Finally, in step 506 each estimated signal is updated with the associated measured signal. The process of updating may vary from tracking filter to tracking filter, and is well-known in the art. However, in most filters a weighted average of the estimated and measured value is found. The weights assigned to the estimated and measured values depend on the tracking filter and confidence in the accuracy of the estimated and measured values. The values of the update are then used as the input to estimate step 502 upon the next iteration. In this way, the estimation is based upon the value of the update in the previous iteration.

Although only one filter is shown, one of ordinary skill will recognize that multiple tracking filters, or any combination of tracking filters, may be used.

According to an embodiment, the steps described above will be repeated for each iteration, or set of measurements, $Z_k$ produced by the signal detector.

The implementation of the Kalman filter is merely illustrative, and is intended to no way limit the scope of the invention. It should be understood that any filter capable of estimating and updating the wavelength and magnitude of a perturbation response signal may be used, including, but not limited to, an Alpha Beta filter, a Particle filter, or an Extended Kalman filter.

The above-described embodiments of the described subject matter can be implemented in any of numerous ways. For example, some embodiments may be implemented using hardware, software, or a combination thereof. When any aspect of an embodiment is implemented at least in part in software, the software code can be executed on any suitable processor or collection of processors, whether provided in a single device or computer or distributed among multiple devices/computers.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein.

Accordingly, it will be appreciated from the foregoing that the embodiments presented represent a significant advancement in the field of perturbation sensors, particularly with respect to tracking signals reflected or transmitted from the perturbation sensors before, during, and after and overlap condition. A detailed embodiment of the invention has been described for the purposes of illustration, but it will be understood that various modifications may be made without departing from the spirit and scope of the invention. Accordingly, the invention is not to be limited except as by the appended claims.

Now will be described the details of an implementation the tracking filter as a Kalman filter for tracking the reflected or transmitted signals of a plurality of perturbation sensors. In the embodiment described, the Kalman filter is implemented as a Single State Kalman Filter. Each feature is treated as a point mass with dynamics that are generally unknown. All that is available to the sensor monitoring system is a set of feature measurements with associated measurement uncertainty. Each feature is either directly measured or derived. Because a Kalman filter is a recursive estimator, the only required inputs are the estimated state from the previous time step and the current measurement.

A Kalman filter uses a dynamic model, referred to as a plant model, to estimate the motion of the objects being tracked. In this embodiment, the plant can be implemented as a nonlinear function of kinematic variables $$F(t, x, \dot{x}, \ddot{x}, \ldots, w) = 0$$

wherein x, the feature of interest, changes as a function of time t. The overdot appearing above the x variables signifies time derivatives of orders corresponding to the number of dots shown, such that $\dot{x}$ represents the first time derivative of x, and $\ddot{x}$ represents the second time derivative of x; $w \equiv w(t)$ is a random variable representing the uncertainty in the assigned plant model, often referred to as process or plant noise.

Although other features may be tracked, in this embodiment, only the wavelength ($\lambda$) and reflectivity of each response are tracked. Jerk is the term for the third time derivative of a parameter. Accordingly, the state equation for wavelength is modeled as a jerk model, wherein $j \equiv \overline{\lambda}$, shown in state space as $$\frac{d}{dt}\begin{bmatrix} \lambda \\ \dot{\lambda} \\ \ddot{\lambda} \\ \overline{\lambda} \end{bmatrix} = \begin{bmatrix} 0 & 1 & 0 & 0 \\ 0 & 0 & 1 & 0 \\ 0 & 0 & 0 & 1 \\ 0 & 0 & 0 & -\alpha \end{bmatrix} \begin{bmatrix} \lambda \\ \dot{\lambda} \\ \ddot{\lambda} \\ \overline{\lambda} \end{bmatrix} + \begin{bmatrix} 0 \\ 0 \\ 0 \\ 1 \end{bmatrix} w(t)$$

where $\dot{j}(t) = \alpha j(t) + w(t)$ and $w(t)$ is a white noise source. The parameter $\alpha$ is a correlation parameter that can be chosen for different dynamics scenarios. If $\alpha$ is chosen "small," the jerk model is dominated by white noise. On the other hand if $\alpha$ is chosen "large," then the model behaves like a constant acceleration model. The following notation may be used to describe the above set of equations $$\frac{d}{dt}\Lambda = A_\lambda \Lambda + B_\lambda w(t).$$

The state equation for r is a white noise driven velocity model ($v \equiv \dot{\rho}$) shown in state space as, $$\frac{d}{dt}\begin{bmatrix} \rho \\ \dot{\rho} \end{bmatrix} = \begin{bmatrix} 0 & 1 \\ 0 & 0 \end{bmatrix}\begin{bmatrix} \rho \\ \dot{\rho} \end{bmatrix} + \begin{bmatrix} 0 \\ 1 \end{bmatrix} w(t)$$

where the same white noise process is used from above, but the invention is not limited to this choice. Similarly, the dynamics for $\rho$ can be summarized as, $$\frac{d}{dt}P = A_\rho P + B_\rho w(t).$$

These models are combined in block matrix form $$\dot{X} = AX + Bw(t), \text{ where } X \equiv \begin{bmatrix} \Lambda \\ P \end{bmatrix}, A \equiv \begin{bmatrix} A_\lambda & 0 \\ 0 & A_\rho \end{bmatrix}, B \equiv \begin{bmatrix} B_\lambda \\ B_\rho \end{bmatrix}.$$

This resulting model, a six dimensional state space model, can be expanded to include any number of features, each with its own plant.

The measurement vector Z in this case is a two dimensional vector (as described in the above detailed description) which can be related to the state vector X by the following expression, $$Z = HX + V, H = \begin{bmatrix} 1 & 0 & 0 & 0 & 0 & 0 \\ 0 & 0 & 0 & 0 & 1 & 0 \end{bmatrix}$$

where V is the measurement noise vector, which is uncorrelated to the plant process noise.

The pair of equations, $\dot{X} = AX + Bw(t)$ and $Z = HX + V$ are solved using the Kalman filter. The first step is to derive an equivalent discrete set of equations. The discrete forms are iteratively solved for the hidden state vector X by the estimate—update method inherent to the Kalman filter. Since the discretization procedure is well known in the art, only the results are shown here.

The remaining description employs the following notation: $\vec{x}_k$ represents a hidden state variable to be estimated; $\hat{x}_{k|k-1}$ represents the state variable from the estimator step, based on previous (k−1) measurements; $\hat{x}_{k|k}$ represents the updated state estimate based on the most recent $k^{th}$ estimate.

The Kalman filter gives the optimal Bayesian solution to the state estimation problem if the posterior probability distribution function (pdf) $p(\vec{x}_k | Z^k)$ is Gaussian at each time step k. Here $\vec{x}_k$ is the hidden state variable to be estimated and $Z^k \equiv \{\vec{z}_1, \vec{z}_2, \ldots, \vec{z}_k\}$ is the collection of measurement vectors up to and including time step k.

The discrete state propagation is given by $\vec{x}_k = F_k \vec{x}_{k-1} + \vec{\omega}_k$, where $\vec{\omega}_k$ is the Gaussian plant noise with mean $\vec{0}$ and covariance matrix $Q_{k-1}$. The state propagation matrix $F_k$ is unique to the chosen plant model. The discrete measurement state $\vec{z}_k = H_k \vec{x}_k + \vec{v}_k$ where is $\vec{v}_k$ the Gaussian measurement uncertainty with mean $\vec{0}$ and covariance matrix $R_k$.

To start the Kalman filter, an a priori state estimate is chosen such that $\hat{x}_{0|0}$ is Gaussian with covariance matrix $P_{0|0}$ and nonzero mean. In an exemplary embodiment, the average of the first N measurements with variance on the order of the spacing between perturbation sensors 104 squared is calculated. On the $k^{th}$ iteration the predictor step of the Kalman filter is given by $\hat{x}_{k|k-1} = F_k \hat{x}_{k-1|k-1}$, with updated covariance $P_{k|k-1} = F_k P_{k-1|k-1} F_k^T + Q_{k-1}$. Prior to using the latest measurement, a measurement prediction is calculated as $\hat{z}_{k|k-1} = H_k \hat{x}_{k|k-1}$ with measurement predicted error given by $S_k = H_k P_{k|k-1} H_k^T + R_k$.

On each iteration there corresponds to each estimator step an update step described here, where a new measurement $\vec{z}_k$ is introduced. The difference between the new measurement and the predicted measurement is known as the innovation $\vec{v}_k \equiv \vec{z}_k - \vec{z}_{k|k-1}$. The innovation is also central to the problem of tracking during overlap. It is used to decide which of all possible hypotheses is to be used to update each track.

The Kalman gain is essential to the corrector step and is derived as $K_k = P_{k|k-1} H_k^T S^{-1}_k$. Given the Kalman gain and innovation updates to state vector $\hat{x}_{k|k}$ and its covariance $P_{k|k}$ are given by $\hat{x}_{k|k} = \hat{x}_{k|k-1} + K_k \vec{v}_k$ and $P_{k|k} = P_{k|k-1} - K_k S_k K_k^T$, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for tracking changes in spectral responses caused by changes in an operating environment, the method comprising:

inputting light to a waveguide medium having a plurality of perturbation sensors disposed in a spaced relationship in the waveguide medium so that signals from the plurality of perturbations sensors are not in an overlap state;

receiving a plurality of signals from the plurality of perturbation sensors;

retrieving from the received signals data representing a plurality of signal values, each signal value comprising at least a magnitude value and a wavelength value;

identifying within the plurality of signal values at least a first signal value and a second signal value being in the overlap state, wherein the overlap state occurs when a difference between a first wavelength value of the first signal and a second wavelength value of the second signal is below a predetermined threshold;

in response to identifying the overlap state:
estimating, for at least some of the plurality of perturbation sensors an expected signal value;
associating each expected signal value with a respective signal value from the plurality of signal values;
updating each expected signal value with the an associated signal value; and
iterating estimation of each expected signal value with the updated associated signal value.

2. The method of claim 1, wherein the waveguide medium is an optical fiber.

3. The method of claim 1, wherein the received signals each comprise at least a portion of a full signal.

4. The method of claim 1, further comprising, before the step of associating, the steps of:
substituting the magnitude value of the first signal value with a previously received magnitude of the first received signal; and
substituting the magnitude value of the second signal value with a previously received magnitude of the second received signal.

5. The method of claim 4, further comprising the steps of:
adding to the plurality of signal values a first extended signal value having a wavelength value equal to the wavelength of the first signal value and a magnitude value equal to the previously received magnitude of the second signal value; and
adding to the plurality of signal values a second extended signal value having a wavelength value equal to the wavelength of the second signal value and a magnitude value equal to the previously received magnitude of the first signal value.

6. The method of claim 1, wherein the step of associating comprises the steps of: calculating an error value between each expected signal value and each signal value in the plurality of signal values; and
assigning each expected signal value to the signal value with a smallest error value.

7. The method of claim 6, wherein the step of calculating the error comprises determining an innovation for each expected signal value and each signal value from the plurality of signal values.

8. The method of claim 1, wherein the step of associating comprises the step of:
calculating an error between an expected signal value and any signal value, from the plurality of signal values, within a predetermined interval of the estimated signal; and
assigning the expected signal value to the signal value within the interval with a smallest error.

9. The method of claim 1, wherein the step of identifying the overlapped signals comprises:
determining whether the difference between the wavelength of any signal value from the plurality of signal values and any other signal value from the plurality of values is less than a predetermined value.

10. The method of claim 1, wherein the steps of estimating and updating are each performed by a Kalman filter.

11. The method of claim 1, wherein the steps of estimating and updating are each performed by an alpha beta filter.

12. The method of claim 1, wherein the steps of estimating and updating are each performed by a particle filter.

13. The method of claim 1, wherein each perturbation sensor is a fiber Bragg grating.

14. The method of claim 1, wherein the plurality of perturbation sensors have unique reflection or transmission wavelengths.

15. A device for tracking changes in spectral responses caused by changes in an operating environment, the device comprising:
a waveguide medium having a plurality of perturbation sensors disposed in a spaced relationship in the waveguide medium, configured to input light so that signals from the plurality of perturbations sensors are not in an overlap state; and
a non-transitory storage medium having a tracking filter and an overlap detector, wherein the device is configured to:
receive data representing a plurality of signal values, each signal value having a magnitude value and a wavelength value; wherein the overlap detector is configured to identify within the plurality of signal values, at least a first signal value and a second signal value being in the overlap state, wherein the overlap state occurs when a difference between a first wavelength value of the first signal and a second wavelength value of the second signal is below a predetermined threshold; and
in response to identifying the overlap state the tracking filter is configured to:
estimate, for at least some of the plurality of perturbation sensors, an expected signal value;
associate each expected signal value with a respective signal value from the plurality of signal values;
update each expected signal value with the an associated signal value and iterate estimation of each expected signal value with the updated associated signal value.

16. The device of claim 15, wherein the data is received from signals reflected by the plurality of perturbation sensors and propagated in a waveguide medium.

17. The device of claim 15, wherein the received signals each comprise at least a portion of a full signal.

18. The device of claim 15, wherein the device is, before associating, further configured to:
substitute the magnitude value of the first signal value with a previously received magnitude of the first reflected signal; and
substitute the magnitude value of the second reflected signal with a previously received magnitude of the second reflected signal.

19. The device of claim 18, wherein the device is further configured to:
add to the plurality of signal values a first extended signal value, having a wavelength value equal to the wavelength of the first signal value and a magnitude value equal to the previously received magnitude of the second signal value; and
add to the plurality of signal values a second extended signal value, having a wavelength value equal to the wavelength of the second signal value and a magnitude value equal to the previously received magnitude of the first signal value.

20. The device of claim 15, wherein associating comprises:
calculating an error value between each expected signal value and each signal value in the plurality of signal values; and assigning each expected signal value to the signal value with a smallest error value.

21. The device of claim 20, wherein calculating the error comprises determining an innovation for each expected signal value and at least one signal value from the plurality of signal values.

22. The device of claim 15, wherein associating comprises:
   calculating an error between an expected signal value and any signal value, from the plurality of signal values, within a predetermined interval of the estimated signal; and
   assigning the expected signal value to the signal value within the interval with a smallest error.

23. The device of claim 15, identifying the overlapped signals comprises:
   determining whether the difference between the wavelength of any signal value from the plurality of signal values and any other signal value from the plurality of values is less than a predetermined value.

24. The device of claim 15, wherein the steps of estimating and updating are each performed by a Kalman filter.

25. The device of claim 15, wherein the steps of estimating and updating are each performed by an alpha beta filter.

26. The device of claim 15, wherein the steps of estimating and updating are each performed by a particle filter.

27. The device of claim 15, wherein each of the perturbation sensors is a fiber Bragg grating.

* * * * *